(12) United States Patent
Liu (10) Patent No.: US 8,541,744 B1
(45) Date of Patent: Sep. 24, 2013

(54) METHOD AND APPARATUS FOR WAVELENGTH LOCKING FREE OPTICAL FREQUENCY COMB BASED DIFFERENTIAL ABSORPTION LIDAR

(71) Applicant: Jian Liu, Sunnyvale, CA (US)

(72) Inventor: Jian Liu, Sunnyvale, CA (US)

( * ) Notice: Subject to any disclaimer, the term of this patent is extended or adjusted under 35 U.S.C. 154(b) by 0 days.

(21) Appl. No.: 13/791,924

(22) Filed: Mar. 9, 2013

(51) Int. Cl.
*G01N 21/00* (2006.01)
(52) U.S. Cl.
USPC .................................. 250/339.11; 250/338.5
(58) Field of Classification Search
USPC ......... 250/330, 338.4, 338.5, 339.08, 339.09, 250/339.11, 339.13
See application file for complete search history.

(56) References Cited

U.S. PATENT DOCUMENTS 6,570,893 B1 * 5/2003 Libatique et al. ............... 372/20

* cited by examiner

*Primary Examiner* — Mark R Gaworecki
(74) *Attorney, Agent, or Firm* — Taboada Law Firm, PLLC; John M. Taboada (57) ABSTRACT

Methods and systems for wavelength locking free OFC based DIAL are disclosed, including generating electromagnetic radiation from a mode-locked fiber laser; coupling the electromagnetic radiation to an acousto-optic modulator; coupling the electromagnetic radiation to a power amplifier; collimating and coupling the amplified electromagnetic radiation into a scanner; steering the collimated and amplified electromagnetic radiation onto a target; using a telescope to collect a portion of the backscattered electromagnetic radiation from the target; coupling the collected portion of the backscattered electromagnetic radiation into a DWDM; using a photon counting receiver coupled to the DWDM to measure a multiple OFC on-resonant band intensity and a multiple OFC off-resonant band intensity; and comparing the multiple OFC on-resonant band intensity with the multiple OFC off-resonant band intensity in order to determine one or more concentrations of one or more molecules within the target. Other embodiments are described and claimed.

23 Claims, 10 Drawing Sheets

METHOD AND APPARATUS FOR WAVELENGTH LOCKING FREE OPTICAL FREQUENCY COMB BASED DIFFERENTIAL ABSORPTION LIDAR

I. BACKGROUND

The invention relates generally to the field of differential absorption Lidar (DIAL). More particularly, the invention relates to a method and apparatus for wavelength locking free optical frequency comb based DIAL capable of simultaneously measuring multiple gas components and their concentration variations over distance.

II. SUMMARY

In one respect, disclosed is a differential absorption Lidar comprising: a mode-locked fiber laser, wherein the mode-locked fiber laser generates an electromagnetic radiation, wherein the electromagnetic radiation comprises an optical frequency comb (OFC) with a frequency comb spacing of a pulsed repetition rate of the mode-locked fiber laser; an acousto-optic modulator comprising an input and an output, wherein the electromagnetic radiation is coupled to the input of the acousto-optic modulator and wherein the acousto-optic modulator is configured to down select the pulse repetition rate of the electromagnetic radiation; a power amplifier comprising an input and an output, wherein the input of the power amplifier is coupled to the output of the acousto-optic modulator and wherein the power amplifier is configured to amplify the down selected pulse repetition rate electromagnetic radiation; a collimator comprising an input and an output, wherein the input of the collimator is coupled to the output of the power amplifier and wherein the collimator is configured to collimate the amplified down selected pulse repetition rate electromagnetic radiation; an azimuth and elevation scanner comprising an input and an output, wherein the input of the azimuth and elevation scanner is coupled to the output of the collimator and wherein the azimuth and elevation scanner is configured to steer the collimated amplified down selected pulse repetition rate electromagnetic radiation onto a target; a telescope comprising an input and an output, wherein the input of the telescope is configured to collect electromagnetic radiation backscattered from the target; a Dense Wavelength Division Multiplexer (DWDM) comprising an input and an output, wherein the input of the DWDM is coupled to the output of the telescope; a photon counting receiver, wherein the photon counting receiver is coupled to the output of the DWDM; a signal processing and control unit, wherein the signal processing and control unit is coupled to the photon counting receiver and wherein the signal processing and control unit is configured to synchronize and gate the mode-locked fiber laser, the acousto-optic modulator, and the photon counting receiver; and a computer coupled to the signal processing and control unit, wherein the computer is configured to compare an on-resonant band intensity of the backscattered electromagnetic radiation with an off-resonant band intensity of the backscattered electromagnetic radiation.

In another respect, disclosed is a method for differential absorption Lidar comprising: generating electromagnetic radiation from a mode-locked fiber laser, wherein the electromagnetic radiation comprises an OFC with a frequency comb spacing of a pulsed repetition rate of the mode-locked fiber laser; coupling the electromagnetic radiation from the mode-locked fiber laser to an acousto-optic modulator, wherein the acousto-optic modulator is configured to down select the pulse repetition rate of the electromagnetic radiation; coupling the down selected pulse repetition rate electromagnetic radiation to a power amplifier, wherein the power amplifier is configured to amplify the down selected pulse repetition rate electromagnetic radiation; collimating and coupling the amplified down selected pulse repetition rate electromagnetic radiation into an azimuth and elevation scanner, wherein the azimuth and elevation scanner is configured to steer the collimated amplified down selected pulse repetition rate electromagnetic radiation; steering the collimated and amplified down selected pulse repetition rate electromagnetic radiation onto a target, wherein the target backscatters a portion of the collimated and amplified down selected pulse repetition rate electromagnetic radiation; using a telescope to collect a portion of the backscattered electromagnetic radiation; coupling the collected portion of the backscattered electromagnetic radiation into a DWDM; using a photon counting receiver coupled to the DWDM to measure a multiple OFC on-resonant band intensity and a multiple OFC off-resonant band intensity; and comparing the multiple OFC on-resonant band intensity with the multiple OFC off-resonant band intensity in order to determine one or more concentrations of one or more molecules within the target.

In another respect, disclosed is a method for differential absorption Lidar comprising: generating electromagnetic radiation from a mode-locked fiber laser, wherein the electromagnetic radiation comprises an OFC with a frequency comb spacing of a pulsed repetition rate of the mode-locked fiber laser; coupling the electromagnetic radiation from the mode-locked fiber laser to an acousto-optic modulator, wherein the acousto-optic modulator is configured to down select the pulse repetition rate of the electromagnetic radiation; coupling the down selected pulse repetition rate electromagnetic radiation to a power amplifier, wherein the power amplifier is configured to amplify the down selected pulse repetition rate electromagnetic radiation; collimating and coupling the amplified down selected pulse repetition rate electromagnetic radiation into an azimuth and elevation scanner, wherein the azimuth and elevation scanner is configured to steer the collimated amplified down selected pulse repetition rate electromagnetic radiation; steering the collimated and amplified down selected pulse repetition rate electromagnetic radiation onto a target, wherein the target backscatters a portion of the collimated and amplified down selected pulse repetition rate electromagnetic radiation; using a telescope to collect a portion of the backscattered electromagnetic radiation; coupling the collected portion of the backscattered electromagnetic radiation into a DWDM; using a photon counting receiver coupled to the DWDM to measure a multiple OFC on-resonant band intensity and a multiple OFC off-resonant band intensity; comparing the multiple OFC on-resonant band intensity with the multiple OFC off-resonant band intensity in order to determine one or more concentrations of one or more molecules within the target; and combining multiple channels of electromagnetic radiation in order to determine the one or more concentrations of the one or more molecules within the target as a function of distance.

Numerous additional embodiments are also possible.

III. BRIEF DESCRIPTION OF THE DRAWINGS

Other objects and advantages of the invention may become apparent upon reading the detailed description and upon reference to the accompanying drawings.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

IV. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

To measure the contents of the global atmosphere, such as carbon dioxide ($CO_2$) or methane ($CH_4$), DIAL systems which use conventional coherent and incoherent light detection and ranging (Lidar) methods have been deployed. In these methods, at least two wavelengths are employed to measure a gas content. One of the wavelengths is absorbed by the gas of interest and is named the "on-resonant band." The other wavelength is not absorbed and is named the "off-resonant band." The "off-resonant band" wavelength is close to the "on-resonant band" wavelength. The "off-resonant band" wavelength is used for baseline extraction so that the concentration of the gas of interest can be determined. Since the bandwidth of molecular absorption is usually very narrow (<0.05 nm), a tiny drift of the probe wavelengths can impact the accuracy of measurement and tremendous efforts must be out into the mechanical, thermal, and optics control of the Lidar. Thus to deal with the sensitivity to environmental changes, conventional Lidar techniques require accurate locking of the "on-resonant band" wavelength and the "off-resonant band" wavelength. Additionally, when multiple gas contents in the atmosphere are measured, which is often the case, multiple groups of lasers have to be used with each laser group dedicated to a specific gas only. These additional requirements not only make DIAL systems which use conventional Lidar methods and systems bulky and expensive, but also less robust to environmental changes.

The situation is even more complicated when gas contents are measured over a long distance such as from satellites since the level of gas concentrations varies at different atmospheric layers. As an example, $CO_2$ makes up a very small fraction (0.039%) of the atmosphere near the Earth's surface. However, $CO_2$ content varies significantly within the first 100 feet above the surface of the Earth. In order to measure the abundance of $CO_2$ from a satellite, a DIAL system with eight lasers must be utilized to detect the variation in $CO_2$ content across the entire atmosphere. It is very complicated and costly to achieve accurate control of eight lasers and corresponding data/signal processing for DIAL systems which use conventional Lidar methods and systems.

The methods and apparatuses of the invention described herein may solve these shortcomings as well as others by proposing a novel wavelength locking free optical frequency comb based DIAL capable of measuring chemical composition in the atmosphere. The methods and apparatuses of the invention are also capable of simultaneously measuring multiple gas components and their concentration variations over distance.

Figure 1:
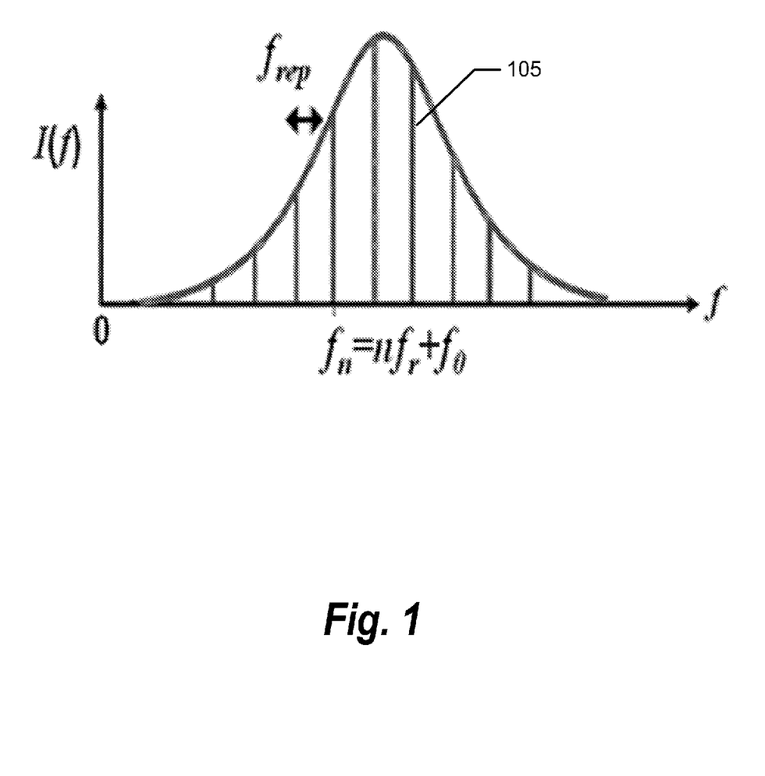
FIG. 1 is a schematic of the frequency comb output for a mode-locked fiber laser, in accordance with some embodiments.

FIG. 1 is a schematic of the frequency comb output for a mode-locked fiber laser, in accordance with some embodiments.

Figure 2:
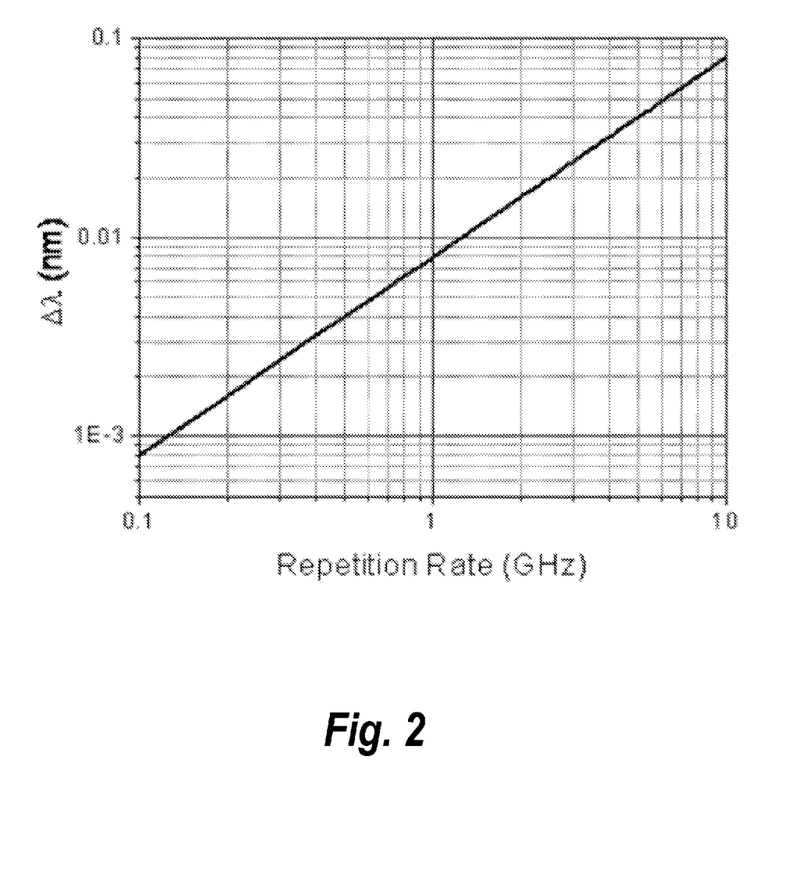
FIG. 2 is a graph of wavelength spacing at 1550 nm between two adjacent modes as a function of laser repetition rate, in accordance with some embodiments.

FIG. 2 is a graph of wavelength spacing at 1550 nm between two adjacent modes as a function of laser repetition rate, in accordance with some embodiments.

In recent years, mode-locked fiber lasers have been shown to produce highly coherent outputs. These sources emit a broad spectrum of light that comprises a set of narrow individual optical lines in frequency space separated by the laser repetition rate, i.e. a frequency comb, as illustrated in FIG. 1. The application of frequency combs has dramatically improved the accuracy of optical frequency measurements. The high range resolution may be obtained due to the broad spectrum and the high Doppler resolution may be obtained due to the narrow line width of each comb tooth. For a wide-bandwidth source, unbalanced dispersion in the signal paths may dramatically degrade the range resolution. The potential problem of ranging resolution is solved by increasing the Doppler sensitivity by dividing the signal wavelengths into multiple channels and taking the average of multiple lines of each individual channel.

The general configuration of a frequency comb is shown in FIG. 1. It is based on a passively mode-locked fiber laser that emits a pulse train in the time domain. This forms a frequency comb in the frequency domain. Each "comb tooth" 105 is a mode of the mode-locked laser. The optical frequency of mode is given by the basic comb equation, $$f_n = nf_r + f_0 \qquad (1)$$

where n is the mode number, $f_r$ is the repetition rate of the mode-locked laser, and $f_0$ is the carrier-envelope offset frequency. The frequency comb from a mode-locked laser spans a spectral region ranging from a few nm to a few tens nm. It may be extended to a much wider spectral range after super-continuum generation, typically from 1 to 2.5 μm. When converted into wavelengths, the wavelength spacing $\Delta\lambda$ between two nearby modes is proportional to the repetition rate $f_r$. The wavelength spacing $\Delta\lambda$ as a function of laser repetition rate is plotted in FIG. 2. For wavelengths around 1550 nm, $\Delta\lambda$ is 0.0008 nm and 0.008 nm at repetition rates of 100 MHz and 1 GHz, respectively. In order to identify the resonant wavelength of $CO_2$ in the proposed DIAL system, we will choose repetition rate of the laser system to be 10 MHz, which can guarantee at least 300 modes (comb teeth) inside an absorption peak with 0.025 nm bandwidth.

Figure 3:
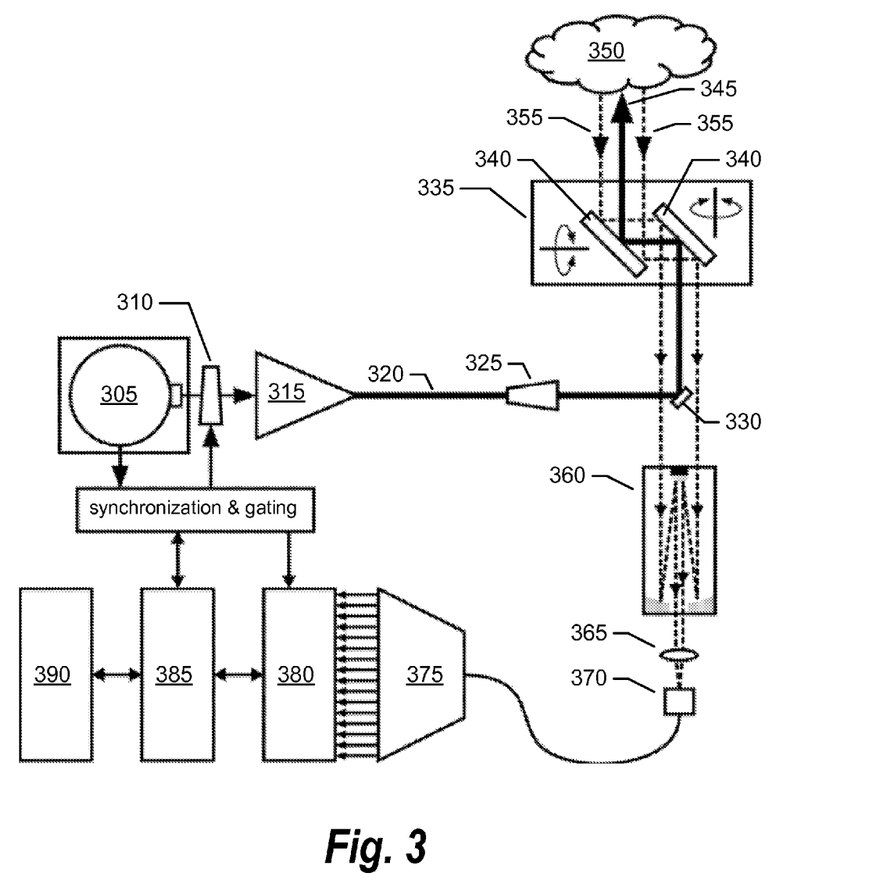
FIG. 3 is a schematic illustration of an optical frequency comb based differential absorption Lidar, in accordance with some embodiments.

FIG. 3 is a schematic illustration of an optical frequency comb based differential absorption Lidar, in accordance with some embodiments.

In some embodiments, the OFC is generated from a mode-locked fiber laser 305 operating at 1 micron, 1.55 micron, 2 micron, 2.8 micron, 3-5 micron, or 7-12 micron spectral regions with a pulse repetition rate (PRR) of 1 to 100 MHz. The mode-locked fiber laser 305 with a repetition rate of 1 to 100 MHz enables sufficient optical frequency comb teeth within the absorption band of many gases (typically between 2 to 3 GHz). An acousto-optic (AO) modulator 310 is used to match the PRR of the mode-locked fiber laser 305 to a PRR of 1 to 100 kHz used in current Lidar systems. The AO modulator 310 is capable of even lower PRR. Next, a power amplifier 315 such as a doped fiber amplifier is used to boost the energy and to expand the OFC spectral range coverage from near IR to mid IR. The doped fiber amplifier may comprise rare earth dopants such as Erbium (Er), Ytterbium (Yb), Thulium (Tm), Holmium (Ho), Er/Yb, Er:ZBLAN, Tm:ZBLAN, Ho:ZBLAN, or a combination of two or more ions. The fiber material may be silica, Germanium, Fluoride, Chalcogenide, ZBLAN, or a combination of two or more similar types of materials. The power amplifier can boost the average power from 1 W to 10 kW and the energy from 1 µJ to 10 mJ with a pulse width less than 0.1 ps (GW peak power, compressed pulse) to 200 ns (stretched pulse) for each interested spectral region. The amplified signal 320 is collimated with a collimator 325 and directed with a mirror 330 into a scanner such as an azimuth and elevation scanner 335. The azimuth and elevation scanner 335 comprises dual oscillating plane mirrors 340 which steer the amplified and collimated probe signal 345 onto a desired target or region 350. The target 350 backscatters a portion of the amplified and collimated probe signal 345. The backscattered light 355 passes back through the azimuth and elevation scanner 335 and is collected by a telescope 360 such as a Schmidt-Cassegrain telescope and coupled with a lens 365 into an optical fiber 370 input of a 3 to 5 GHz bandwidth dense wavelength division multiplexing (DWDM) 375. The DWDM 370 splits the different modes from the optical frequency comb of the mode-locked fiber laser to form a multiple OFC on-resonant band and a multiple OFC off-resonant band. The high peak power of the mode-locked fiber laser 305 makes OFC ideal for single photon detection. The signal from the DWDM 375 is detected with a photon counting receiver 380. The photon counting receiver 380 may comprise a Si/InGaAs/GaAs single photon avalanche photodiode (S-APD) or photo multiplier tubes (PMTs) to detect weak backscattered signal depending on the wavelength channel used. A signal processing and control unit 385 processes the signal from the photon counting receiver 380 and provides feedback to the laser and synchronizes the photon counting receiver 380. The system is controlled by a computer 390 coupled to the signal processing and control unit 385. By comparing between the multiple OFC on-resonant band intensity and the multiple OFC off-resonant band intensity, the concentration of the gases of interest within the target 350 may be extracted and mapped. Since potentially thousands of channels may be used to simultaneously measure multiple gas contents and their distance variations with only a single fiber laser, the wavelength locker for accurate measurement and control of laser wavelength in conventional Lidar methods and systems is not required. The OFC DIAL methods and apparatuses are more reliable than conventional Lidar methods and systems and require minimal effort for daily operation. Additionally, the large spectrum span from near-infrared (NIR) to mid-infrared (MIR) permits the simultaneous monitoring of many different species such as $CO_2$, $CH_4$, carbon monoxide (CO), nitrous oxide ($N_2O$), and water ($H_2O$) as well as the concentration measurement over distances.

Figure 4:
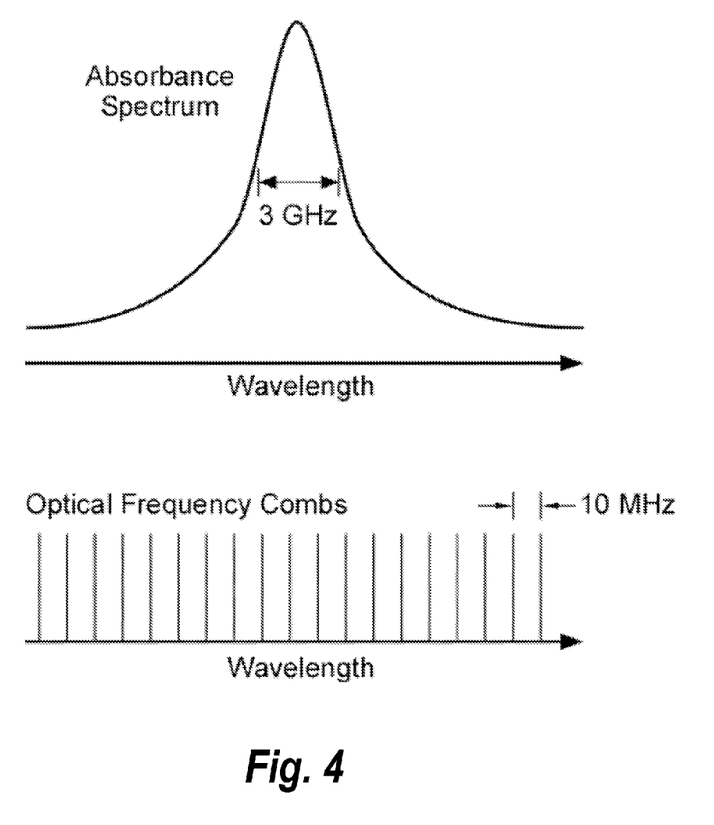
FIG. 4 is schematic illustration of an optical frequency comb coverage of a gas absorption spectrum, in accordance with some embodiments.

FIG. 4 is schematic illustration of an optical frequency comb coverage of a gas absorption spectrum, in accordance with some embodiments.

For a frequency comb spacing of 10 MHz and a spectral bandwidth of a single gas molecular absorption line of about 2 to 3 GHz, over 200 lines or teeth of the OFC are included within the single gas molecular absorption line. Regardless how the laser wavelength drifts or the Doppler effects impact, the selected OFC can self-compensate with its multi-line coverage of the single gas molecular absorption line. Looking at it another way, since each OFC line has a linewidth from several kHz to sub-hertz, it is equivalent to a simultaneous measurement using hundreds of narrow-linewidth single frequency lasers with automatic locked frequency. For example, the absorption peak of $CO_2$ at 1580.35 nm has the bandwidth of 0.025 nm (or 3 GHz) and adjacent absorption peaks have a spacing of 0.4 nm (50 GHz). Using a 10 MHz mode-locked laser OFC that has OFC spacing of 10 MHz as shown in FIG. 4, there will be at least three hundred lines (teeth) inside the 3 GHz absorption spectrum bandwidth. Assuming a 5 GHz optical filter is used, the bandwidth is large enough to compensate the laser wavelength drift and Doppler effects. Moreover, the peak power of each single line can be amplified to over 100 kW, thus providing for long distance measurement with high sensitivity and accuracy, by combining with S-APD. In addition to the three hundred OFC teeth inside the absorption spectrum peak, an off resonance OFC band is measured as a baseline reference. Using the example of $CO_2$ at 1580.35 nm, a DWDM with a bandwidth of 5 GHz may be used to separate on- and off-resonance DIAL bands. The absorbance can be calculated from the difference between the on- and off-resonance DIAL bands, thus the gas concentration at a particular location may be obtained. By combining multiple channels such as 1570 nm, 1572 nm, 2000 nm, and 2020 nm to probe the different $CO_2$ absorption levels, the $CO_2$ concentration may be measured as a function of distance.

Figure 5:
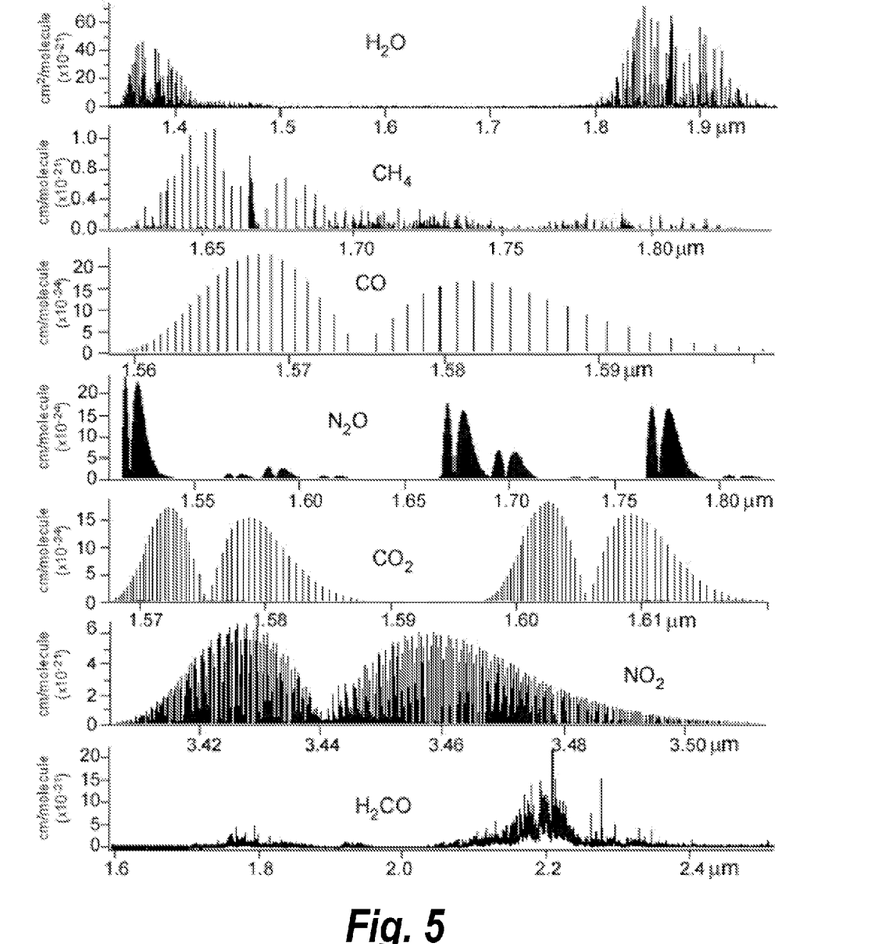
FIG. 5 are graphs showing the absorption spectra of typical chemical composition in Earth's atmosphere, in accordance with some embodiments.

FIG. 5 are graphs showing the absorption spectra of typical chemical composition in Earth's atmosphere, in accordance with some embodiments.

The broadband OFC DIAL system disclosed in FIG. 3 is capable of measuring absorption lines from various atmospheric molecules with absorption peaks between 1 and 2.5 µm. Using an optical parametric oscillator (OPO) or optical parametric amplifier (OPA) or chalcogenide fiber, the spectrum can be further extended to 3 to 5 µm (mid wave infrared, MWIR) or 7 to 12 µm (long wave infrared, LWIR). In this embodiment, a matured silica fiber laser based OFC (1 µm and 2.5 µm) is used as an example. Such products, the Uranus and Pluto series (www.polaronyx.com), are currently commercially available from PolarOnyx, Inc. An AO modulator is used to down select the PRR of the mode-locked fiber laser from 10 MHz to 1-100 kHz in order to match the PRR of most current DIAL systems. It is also possible to add an extra AO pulse picker to reduce the PRR to even lower Hz levels. FIG. 5 shows the absorption spectra for $H_2O$, $CH_4$, CO, $N_2O$, $CO_2$, nitrogen dioxide ($NO_2$), and formaldehyde ($H_2CO$). The broadband OFC DIAL system disclosed in FIG. 3 is capable of individually or simultaneously measuring the absorption of these molecules.

Figure 6A:
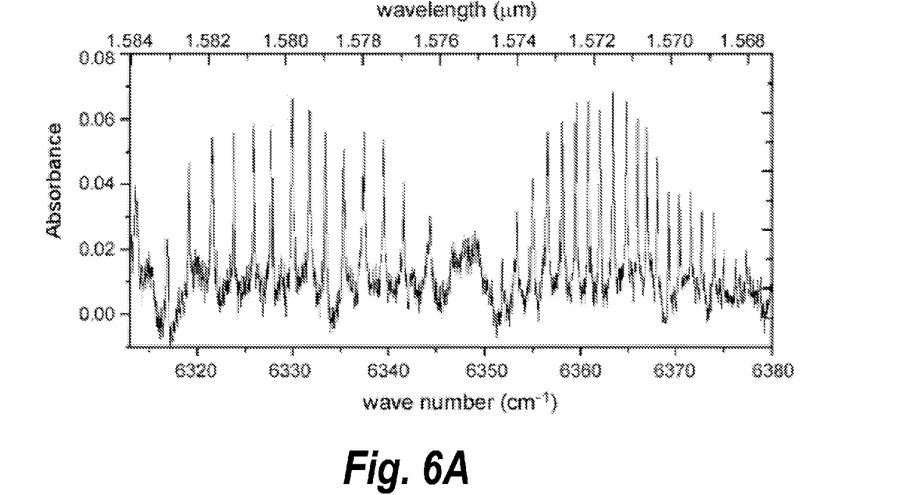
FIGS. 6A, B, and C are graphs showing the absorption spectra of $CO_2$, in accordance with some embodiments.
Figure 6B:
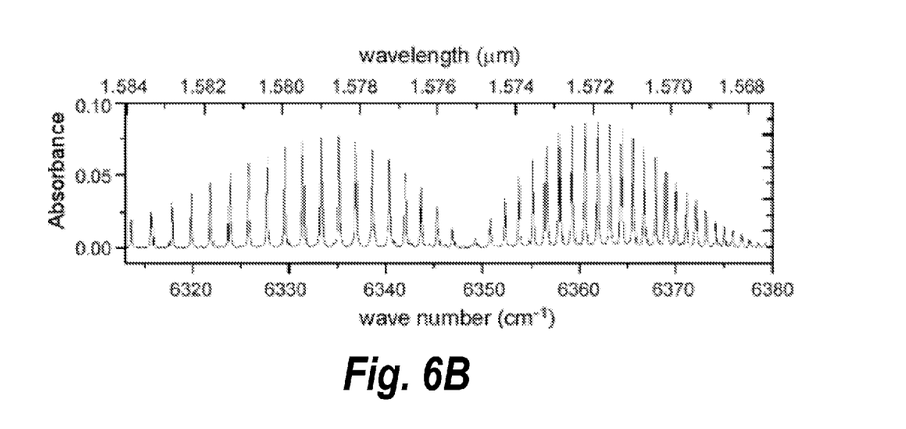
Figure 6C:
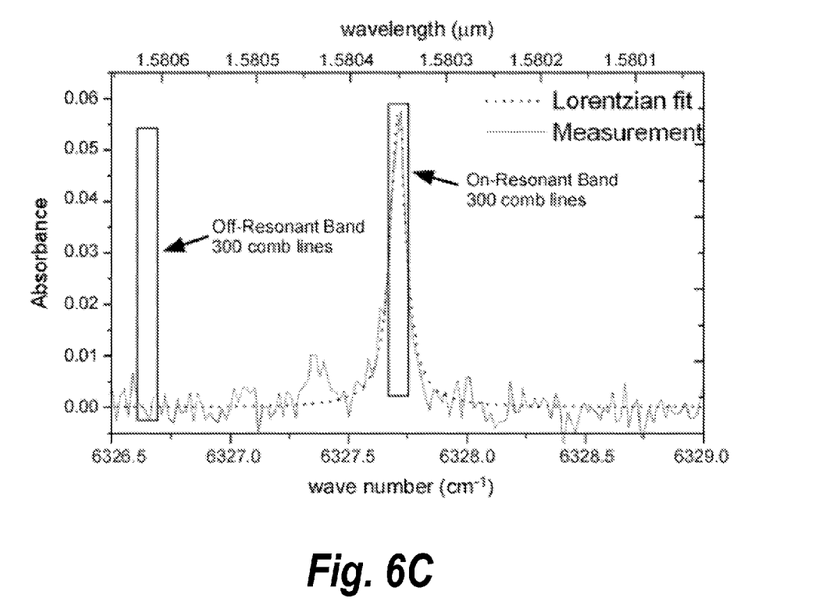

FIGS. 6A, B, and C are graphs showing the absorption spectra of $CO_2$, in accordance with some embodiments.

Carbon dioxide is one of the most critical green house gases and its accurate measurement in the atmosphere is essential. Carbon dioxide has many absorption peaks around 1570 nm and 2020 nm. As an example, the absorption peak around 1570 nm can be seen in FIG. 6A which shows the measured high resolution absorption spectra of $CO_2$. FIG. 6B shows the model calculation for the absorption spectra of $CO_2$. FIG. 6C shows a representative absorption peak of $CO_2$ around 1.58 µm. The bandwidth of the absorption peak of FIG. 6C is only about 0.025 nm (or 3 GHz). Adjacent absorption peaks are separated by about 0.4 nm (50 GHz). For conventional differential absorption Lidar, the on-resonant wavelength must be locked to the exact resonant wavelength that has the maximum absorption efficiency in order to precisely measure the concentration. In contrast, for a wavelength locking free optical frequency comb based differential absorption Lidar with uniformly spaced frequency combs having a frequency spacing of 10 MHz, there are over 300 comb lines within the bandwidth of the representative absorption peak of $CO_2$ at 1580.35 nm shown in FIG. 6C. The averaged power from these 300 comb lines (as opposed to a single line) will compensate any type of laser and environmental variations. This compensation mechanism makes it unnecessary to control each individual line accurately. By using a standard telecom DWDM product with a 6 GHz bandwidth and 50 GHz channel spacing for example, the on-resonant band and off-resonant band can be easily separated. Additionally, by combining multiple channels such as 1570 nm, 1572 nm, 2000 nm, 2020 nm, etc. at different $CO_2$ absorption levels, the $CO_2$ concentration as a function of distance may be measured. Selecting different bands of OFC allows the measurement of multiple atmospheric contents such as 1650 nm band for $CH_4$, 1850 nm band for $H_2O$, 3430 nm band for $NO_2$, 2200 nm band for $H_2CO$, and so on as shown in FIG. 5.

Figure 7:
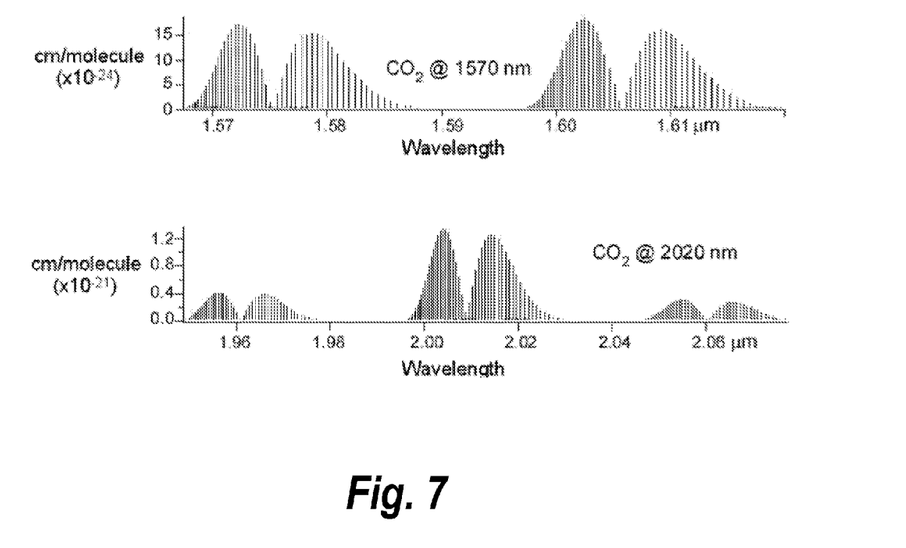
FIG. 7 are graphs showing the absorption spectra of $CO_2$ at 1570 nm and 2020 nm, in accordance with some embodiments.

FIG. 7 are graphs showing the absorption spectra of $CO_2$ at 1570 nm and 2020 nm, in accordance with some embodiments.

Figure 8:
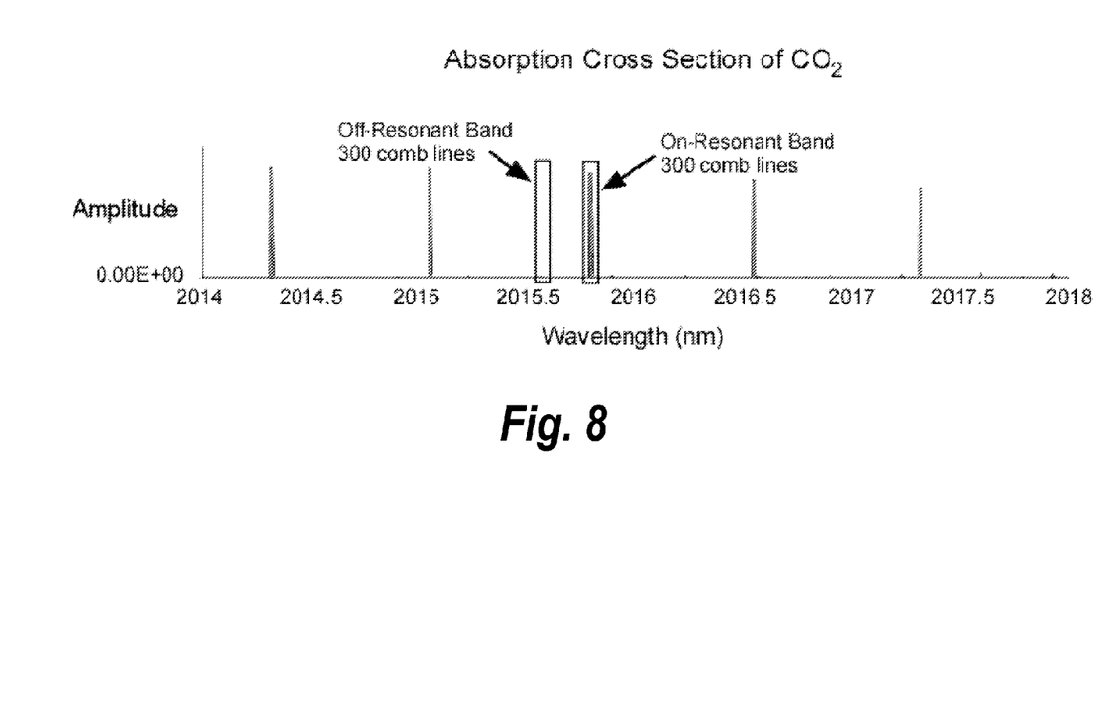
FIG. 8 is a graph showing the on-resonant band and off-resonant band of the absorption spectra of $CO_2$ at about 2016 nm, in accordance with some embodiments.

FIG. 8 is a graph showing the on-resonant band and off-resonant band of the absorption spectra of $CO_2$ at about 2016 nm, in accordance with some embodiments.

In an alternative embodiment, a 2 micron mode-locked fiber laser may be used to probe for the 2 micron absorbance of $CO_2$. FIG. 7 shows that the absorption at 2 µm is roughly three orders of magnitude higher than the absorption at 1.57 µm. FIG. 8 shows a representative absorption peak of $CO_2$ in the 2 µm range. The bandwidth of the individual absorption peak is only about 0.04 nm (or 3 GHz) and adjacent peaks are separated by 0.8 nm (65 GHz) at 2015 nm. For conventional differential absorption Lidar, the on-resonant wavelength must be locked to the exact resonant wavelength that has the maximum absorption efficiency in order to precisely measure the concentration. In contrast, for a wavelength locking free optical frequency comb based differential absorption Lidar with uniformly spaced frequency combs with a frequency spacing of 10 MHz, there are over 300 comb lines within the bandwidth of the representative absorption peak of $CO_2$ at 2015 nm shown in FIG. 8. The averaged power from these 300 comb lines (as opposed to a single line) will compensate any type of laser and environmental variations. This compensation mechanism makes it unnecessary to control each individual line accurately. By using a standard telecom DWDM product (or technology) with a 6 GHz bandwidth and 50 GHz channel spacing for example, the on-resonant band and off-resonant band can be easily separated. Additionally, by combining multiple channels such as 2013 nm, 2015 nm, 2018 nm, and 2020 nm, etc. at different $CO_2$ absorption levels, the $CO_2$ concentration as a function of distance may be measured.

Figure 9:
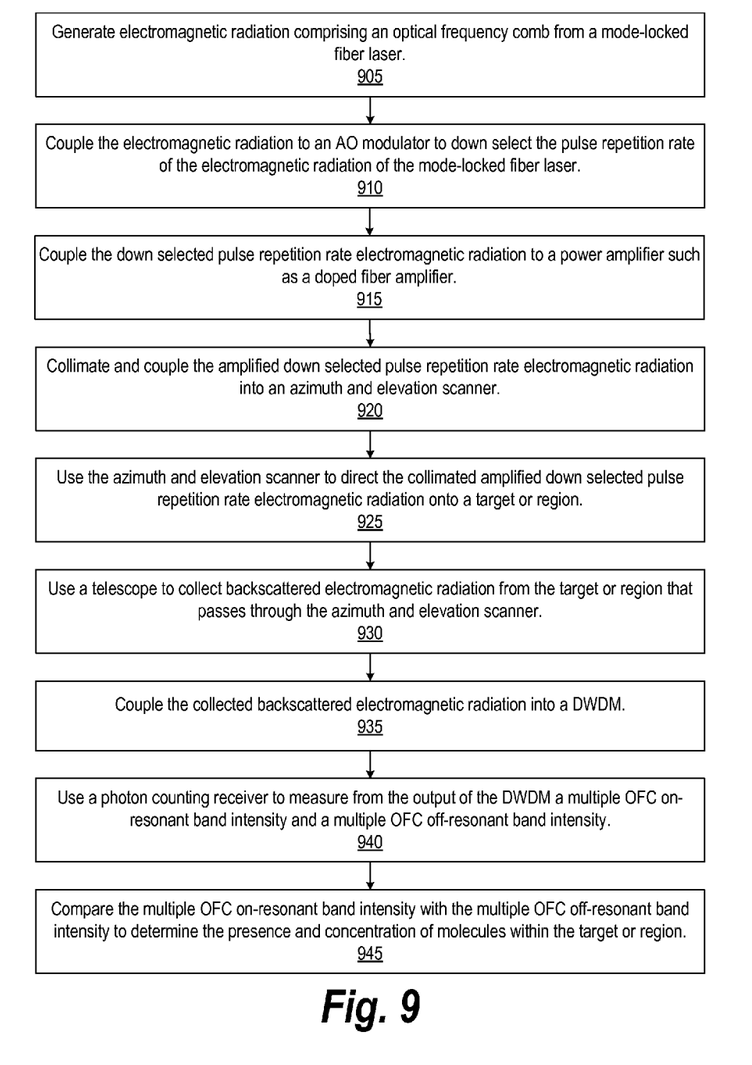
FIG. 9 is a block diagram illustrating a method for wavelength locking free optical frequency comb based differential absorption Lidar, in accordance with some embodiments.

FIG. 9 is a block diagram illustrating a method for wavelength locking free optical frequency comb based differential absorption Lidar, in accordance with some embodiments.

In some embodiments, processing begins at step 905 where a mode-locked fiber laser is used to generate electromagnetic radiation comprising an optical frequency comb. At step 910, the electromagnetic radiation is coupled into an AO modulator to down select the pulse repetition rate of the electromagnetic radiation of the mode-locked fiber laser. At step 915, the down selected pulse repetition rate electromagnetic radiation is then coupled to a power amplifier such as a doped fiber amplifier. The doped fiber amplifier may comprise rare earth dopants such as Erbium (Er), Ytterbium (Yb), Thulium (Tm), Holmium (Ho), Er/Yb, Er:ZBLAN, Tm:ZBLAN, Ho:ZBLAN, or a combination of two or more ions. The fiber material may be silica, Germanium, Fluoride, Chalcogenide, ZBLAN, or a combination of two or more similar types of materials. Using an optical parametric oscillator (OPO) or optical parametric amplifier (OPA) or chalcogenide fiber, the spectrum can be further extended to 3 to 5 µm (mid wave infrared, MWIR) or 7 to 12 µm (long wave infrared, LWIR). At step 920, the amplified down selected pulse repetition rate electromagnetic radiation is then collimated and coupled into an azimuth and elevation scanner. The azimuth and elevation scanner directs the collimated amplified down selected pulse repetition rate electromagnetic radiation onto a desired target or region. At step 930, a telescope such as a Schmidt-Cassegrain telescope is then used to collect backscattered electromagnetic radiation from the target or region that passes through the azimuth and elevation scanner. At step 935, the collected backscattered electromagnetic radiation is then coupled into a DWDM. The DWDM splits the modes from the optical frequency comb of the mode-locked fiber laser to form a multiple OFC on-resonant band and a multiple OFC off-resonant band. At step 940, a photon counting receiver is used to measure the multiple OFC on-resonant band intensity and the multiple OFC off-resonant band intensity. At step 945, the multiple OFC on-resonant band intensity is compared with the multiple OFC off-resonant band intensity to determine the presence and concentration of molecules of interest, such as gases, within the target.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

The invention claimed is:

1. A differential absorption Lidar comprising:
a mode-locked fiber laser, wherein the mode-locked fiber laser generates an electromagnetic radiation, wherein the electromagnetic radiation comprises an optical frequency comb with a frequency comb spacing of a pulsed repetition rate of the mode-locked fiber laser;
an acousto-optic modulator comprising an input and an output, wherein the electromagnetic radiation is coupled to the input of the acousto-optic modulator and wherein the acousto-optic modulator is configured to down select the pulse repetition rate of the electromagnetic radiation;
a power amplifier comprising an input and an output, wherein the input of the power amplifier is coupled to the output of the acousto-optic modulator and wherein the power amplifier is configured to amplify the down selected pulse repetition rate electromagnetic radiation;
a collimator comprising an input and an output, wherein the input of the collimator is coupled to the output of the power amplifier and wherein the collimator is configured to collimate the amplified down selected pulse repetition rate electromagnetic radiation;
an azimuth and elevation scanner comprising an input and an output, wherein the input of the azimuth and elevation scanner is coupled to the output of the collimator and wherein the azimuth and elevation scanner is configured to steer the collimated amplified down selected pulse repetition rate electromagnetic radiation onto a target;
a telescope comprising an input and an output, wherein the input of the telescope is configured to collect electromagnetic radiation backscattered from the target;
a DWDM comprising an input and an output, wherein the input of the DWDM is coupled to the output of the telescope;
a photon counting receiver, wherein the photon counting receiver is coupled to the output of the DWDM;
a signal processing and control unit, wherein the signal processing and control unit is coupled to the photon counting receiver and wherein the signal processing and control unit is configured to synchronize and gate the mode-locked fiber laser, the acousto-optic modulator, and the photon counting receiver; and
a computer coupled to the signal processing and control unit, wherein the computer is configured to compare an on-resonant band intensity of the backscattered electromagnetic radiation with an off-resonant band intensity of the backscattered electromagnetic radiation.

2. The differential absorption Lidar of claim 1, wherein the pulse repetition rate of the electromagnetic radiation generated from the mode-locked fiber laser ranges from about 1 to 100 MHz.

3. The differential absorption Lidar of claim 1, wherein the pulse repetition rate of the down selected electromagnetic radiation ranges from about 1 to 100 kHz.

4. The differential absorption Lidar of claim 1, wherein the amplified down selected pulse repetition rate electromagnetic radiation comprises:
a power greater than about 1 W;
an energy greater than about 1 µJ; and
a pulse width from 0.1 ps to 200 ns.

5. The differential absorption Lidar of claim 1, wherein the azimuth and elevation scanner comprises dual oscillating plane mirrors.

6. The differential absorption Lidar of claim 1, wherein the photon counting receiver comprises a single photon avalanche photodiode or a photomultiplier tube.

7. The differential absorption Lidar of claim 1, wherein the power amplifier comprises a doped fiber amplifier.

8. The differential absorption Lidar of claim 7, wherein the doped fiber amplifier comprises a doped gain medium comprising at least one of: Er, Yb, Tm, Ho, Er/Yb, Er:ZBLAN, Ho:ZBLAN, and Tm:ZBLAN.

9. The differential absorption Lidar of claim 7, wherein the doped fiber amplifier comprises a fiber material comprising at least one of: silica, Germanium, Fluoride, Chalcogenide, and ZBLAN.

10. The differential absorption Lidar of claim 1, further comprising an OPO and/or an OPA, wherein the OPO and/or the OPA are configured to extend spectral wavelength ranges of the electromagnetic radiation.

11. The differential absorption Lidar of claim 1, wherein the amplified down selected pulse repetition rate electromagnetic radiation spans from NIR to MWIR and/or LWIR.

12. A method for differential absorption Lidar comprising:
generating electromagnetic radiation from a mode-locked fiber laser, wherein the electromagnetic radiation comprises an optical frequency comb with a frequency comb spacing of a pulsed repetition rate of the mode-locked fiber laser;
coupling the electromagnetic radiation from the mode-locked fiber laser to an acousto-optic modulator, wherein the acousto-optic modulator is configured to down select the pulse repetition rate of the electromagnetic radiation;
coupling the down selected pulse repetition rate electromagnetic radiation to a power amplifier, wherein the power amplifier is configured to amplify the down selected pulse repetition rate electromagnetic radiation;
collimating and coupling the amplified down selected pulse repetition rate electromagnetic radiation into an azimuth and elevation scanner, wherein the azimuth and elevation scanner is configured to steer the collimated amplified down selected pulse repetition rate electromagnetic radiation;
steering the collimated and amplified down selected pulse repetition rate electromagnetic radiation onto a target, wherein the target backscatters a portion of the collimated and amplified down selected pulse repetition rate electromagnetic radiation;
using a telescope to collect a portion of the backscattered electromagnetic radiation;
coupling the collected portion of the backscattered electromagnetic radiation into a DWDM;
using a photon counting receiver coupled to the DWDM to measure a multiple OFC on-resonant band intensity and a multiple OFC off-resonant band intensity; and
comparing the multiple OFC on-resonant band intensity with the multiple OFC off-resonant band intensity in order to determine one or more concentrations of one or more molecules within the target.

13. The method of claim 12 further comprising combining multiple channels of electromagnetic radiation in order to determine the one or more concentrations of the one or more molecules within the target as a function of distance.

14. The method of claim 12, wherein the pulse repetition rate of the electromagnetic radiation generated from the mode-locked fiber laser ranges from about 1 to 100 MHz.

15. The method of claim 12, wherein the pulse repetition rate of the down selected electromagnetic radiation ranges from about 1 to 100 kHz.

16. The method of claim 12, wherein the amplified down selected pulse repetition rate electromagnetic radiation comprises:
a power greater than about 1 W;
an energy greater than about 1 µJ; and
a pulse width from 0.1 ps to 200 ns.

17. The method of claim 12, wherein the azimuth and elevation scanner comprises dual oscillating plane mirrors.

18. The method of claim 12, wherein the photon counting receiver comprises a single photon avalanche photodiode or a photomultiplier tube.

19. The method of claim 12, wherein the power amplifier comprises a doped fiber amplifier.

20. The method of claim 19, wherein the doped fiber amplifier comprises a doped gain medium comprising at least one of: Er, Yb, Tm, Ho, Er/Yb, Er:ZBLAN, Ho:ZBLAN, and Tm:ZBLAN.

21. The method of claim 19, wherein the doped fiber amplifier comprises a fiber material comprising at least one of: silica, Germanium, Fluoride, Chalcogenide, and ZBLAN.

22. The method of claim 12 further comprising using an OPO and/or an OPA to extend spectral wavelength ranges of the electromagnetic radiation.

23. The method of claim 12, wherein the amplified down selected pulse repetition rate electromagnetic radiation spans from NIR to MWIR and/or LWIR.

* * * * *